US010835639B1

(12) United States Patent
Francis et al.

(10) Patent No.: US 10,835,639 B1
(45) Date of Patent: Nov. 17, 2020

(54) BIOPOLYMER COMPOSITIONS, SCAFFOLDS AND DEVICES

(71) Applicant: EMBODY INC., Norfolk, VA (US)

(72) Inventors: Michael Francis, Norfolk, VA (US); Nathan Kemper, Norfolk, VA (US); Hilary Wriggers, Norfolk, VA (US)

(73) Assignee: EMBODY INC., Norfolk, VA (US)

( * ) Notice: Subject to any disclaimer, the term of this patent is extended or adjusted under 35 U.S.C. 154(b) by 0 days.

(21) Appl. No.: 16/818,241

(22) Filed: Mar. 13, 2020

Related U.S. Application Data

(60) Division of application No. 16/152,963, filed on Oct. 5, 2018, now Pat. No. 10,617,787, which is a continuation of application No. PCT/US2018/000119, filed on May 15, 2018.

(60) Provisional application No. 62/603,026, filed on May 16, 2017.

(51) Int. Cl.
*A61L 27/18* (2006.01)
*A61L 27/38* (2006.01)
*A61L 27/54* (2006.01)
*A61L 27/58* (2006.01)
*A61L 27/44* (2006.01)
*A61L 27/26* (2006.01)
*A61L 27/24* (2006.01)
*A61K 38/39* (2006.01)
*A61K 47/34* (2017.01)
*A61K 9/00* (2006.01)

(52) U.S. Cl.
CPC .......... *A61L 27/18* (2013.01); *A61K 9/0024* (2013.01); *A61K 38/39* (2013.01); *A61K 47/34* (2013.01); *A61L 27/24* (2013.01); *A61L 27/26* (2013.01); *A61L 27/3804* (2013.01); *A61L 27/386* (2013.01); *A61L 27/44* (2013.01); *A61L 27/54* (2013.01); *A61L 27/58* (2013.01); *A61L 2300/604* (2013.01); *A61L 2300/64* (2013.01); *A61L 2400/12* (2013.01); *A61L 2430/10* (2013.01); *A61L 2430/34* (2013.01)

(58) Field of Classification Search
CPC .......... A61L 27/18; A61L 27/24; A61L 27/26; A61L 27/3804
See application file for complete search history.

(56) References Cited

U.S. PATENT DOCUMENTS

| 5,171,273 | A  | 12/1992 | Silver et al. |
| 7,862,831 | B2 | 1/2011  | Wang et al. |
| 7,878,786 | B2 | 2/2011  | Yost et al. |
| 8,048,361 | B2 | 11/2011 | Wang et al. |
| 8,491,457 | B2 | 7/2013  | Atala et al. |
| 8,585,753 | B2 | 11/2013 | Scanlon et al. |
| 8,586,345 | B2 | 11/2013 | Simpson et al. |
| 8,697,044 | B2 | 4/2014  | Schroeder et al. |
| 9,034,239 | B2 | 5/2015  | Yun et al. |
| 9,198,750 | B2 | 12/2015 | Van Kampen et al. |
| 9,393,104 | B2 | 7/2016  | Kampen et al. |
| 9,421,305 | B2 | 8/2016  | Lee et al. |
| 9,597,430 | B2 | 3/2017  | Ratcliffe et al. |
| 9,683,011 | B2 | 6/2017  | Wnek et al. |
| 9,757,132 | B2 | 9/2017  | Laurencin et al. |
| 2002/0090725 | A1 | 7/2002 | Simpson et al. |
| 2002/0100725 | A1 | 8/2002 | Lee et al. |
| 2003/0105528 | A1 | 6/2003 | Shimp et al. |
| 2003/0114937 | A1 | 6/2003 | Leatherbury et al. |
| 2005/0008675 | A1 | 1/2005 | Bhatia et al. |
| 2005/0113938 | A1 | 5/2005 | Jamiolkowski et al. |
| 2006/0154063 | A1 | 7/2006 | Fujihara et al. |
| 2006/0204539 | A1 | 9/2006 | Atala et al. |
| 2007/0269481 | A1 | 11/2007 | Li et al. |
| 2008/0051888 | A1 | 2/2008 | Ratcliffe et al. |
| 2008/0188936 | A1 | 8/2008 | Ball et al. |
| 2009/0098175 | A1 | 4/2009 | Buehrer et al. |
| 2009/0202430 | A1 | 8/2009 | Hoemann et al. |
| 2009/0202616 | A1 | 8/2009 | Chong et al. |
| 2009/0240342 | A1 | 9/2009 | Lindh, Sr. et al. |
| 2010/0063599 | A1 | 3/2010 | Brunelle et al. |
| 2010/0145367 | A1 | 6/2010 | Ratcliffe |
| 2010/0191332 | A1 | 7/2010 | Euteneuer et al. |
| 2010/0291058 | A1 | 11/2010 | Bowlin et al. |
| 2010/0292791 | A1 | 11/2010 | Lu et al. |
| 2010/0331980 | A1 | 12/2010 | Lee et al. |
| 2011/0224702 | A1 | 9/2011 | Van Kempen et al. |
| 2011/0238178 | A1 | 9/2011 | Downes et al. |
| 2011/0293685 | A1 | 12/2011 | Kuo et al. |
| 2012/0273993 | A1 | 11/2012 | Shoseyov et al. |

(Continued)

FOREIGN PATENT DOCUMENTS

| CN | 1596996 A | 3/2005 |
| CN | 107261210 A | 10/2017 |

(Continued)

OTHER PUBLICATIONS

Cheng et al., "Isolation, Characterization and Evaluation of Collagen from Jellyfish *Rhopilema esculentum* Kishinouye for Use in Hemostatic Applications", PLoS ONE 12(1), Jan. 19, 2017, pp. 1-21.

Hochleitner et al., "Melt electrowriting below the critical translation speed to fabricate crimped elastomer scaffolds with non-linear extension behaviour mimicking that of ligaments and tendons", Acta Biomaterialia 72 (2018) 110-120.

Hochleitner et al., "Melt Electrowriting of Thermoplastic Elastomers", Macromolecular Rapid Communications, 2018, 39, 1800055, pp. 1-7.

(Continued)

Primary Examiner — Jianfeng Song
(74) Attorney, Agent, or Firm — J.A. Lindeman & Co. PLLC

(57) ABSTRACT

Compositions and blends of biopolymers and copolymers are described, along with their use to prepare biocompatible scaffolds and surgically implantable devices for use in supporting and facilitating the repair of soft tissue injuries.

2 Claims, No Drawings

(56) References Cited

U.S. PATENT DOCUMENTS

| | | |
|---|---|---|
| 2013/0095167 A1 | 4/2013 | Warnke |
| 2013/0149532 A1 | 6/2013 | Yun et al. |
| 2014/0011416 A1 | 1/2014 | Yang et al. |
| 2014/0051169 A1 | 2/2014 | Ganey et al. |
| 2014/0112973 A1 | 4/2014 | Steinberg et al. |
| 2015/0045454 A1 | 2/2015 | Kong et al. |
| 2015/0081000 A1 | 3/2015 | Hossainy et al. |
| 2015/0086607 A1 | 3/2015 | Johnson et al. |
| 2015/0230918 A1 | 8/2015 | Detamore et al. |
| 2015/0367030 A1 | 12/2015 | Murray |
| 2016/0015852 A1 | 1/2016 | Liou et al. |
| 2016/0022865 A1* | 1/2016 | Francis ............ A61L 27/3604 424/569 |
| 2016/0068654 A1 | 3/2016 | Huh et al. |
| 2016/0106548 A1 | 4/2016 | Li et al. |
| 2016/0130558 A1 | 5/2016 | Baer |
| 2016/0136895 A1 | 5/2016 | Beyer et al. |
| 2016/0263280 A1 | 9/2016 | Harrell |
| 2016/0279219 A1 | 9/2016 | Mooney et al. |
| 2016/0279301 A1 | 9/2016 | He et al. |
| 2016/0287374 A1 | 10/2016 | Soletti et al. |
| 2016/0296627 A1 | 10/2016 | Garcia et al. |
| 2016/0317281 A1 | 11/2016 | Van Kampen et al. |
| 2016/0325013 A1 | 11/2016 | Li et al. |
| 2016/0325022 A1 | 11/2016 | Liu et al. |
| 2017/0233834 A1 | 8/2017 | Purcell et al. |
| 2017/0273775 A1 | 9/2017 | Rocco et al. |
| 2018/0193524 A1 | 7/2018 | Shoseyov et al. |
| 2018/0368982 A1 | 12/2018 | Ball |

FOREIGN PATENT DOCUMENTS

| | | |
|---|---|---|
| EP | 2322234 B1 | 9/2005 |
| EP | 1216296 B1 | 4/2009 |
| EP | 1863547 B1 | 5/2016 |
| WO | 98/30252 A1 | 7/1998 |
| WO | 99/39724 A1 | 8/1999 |
| WO | 2007109304 A2 | 9/2007 |
| WO | 2008131293 A2 | 10/2008 |
| WO | 2009079211 A1 | 6/2009 |
| WO | 2009/149181 A2 | 12/2009 |
| WO | 2013/093921 A1 | 6/2013 |
| WO | 2013123147 A1 | 8/2013 |
| WO | 2013/172788 A1 | 11/2013 |
| WO | 2015/138970 A1 | 9/2015 |
| WO | 2016/042211 A1 | 3/2016 |
| WO | 2016/156992 A2 | 10/2016 |
| WO | 2017053757 A1 | 3/2017 |
| WO | 2018092098 A1 | 5/2018 |
| WO | 2018/212792 A2 | 11/2018 |
| WO | 2018212792 A2 | 11/2018 |

OTHER PUBLICATIONS

Hoque et al., "Extrusion Based Rapid Prototyping Technique: An Advanced Platform for Tissue Engineering Scaffold Fabrication", Aug. 9, 2011, Biopolymers vol. 97, No. 2, pp. 83-93.

Hrynevich et al., "Dimension-Based Design of Melt Electrowritten Scaffolds", Nano-Micro Small, 2018, 14, 1800232, pp. 1-6.

Huang et al., "A review on polymer nanofibers by electrospinning and their applications in nanocomposites", Composites Science and Technology 63 (2003) 2223-2253.

Jha et al., "Electrospun Collagen: A Tissue Engineering Scaffold with Unique Functional Properties in aWide Variety of Applications", Journal of Nanomaterials, vol. 2011, Article ID 348268, pp. 1-15.

Krishnamoorthi et al., "Isolation and partial characterization of collagen from outer skin of Sepia pharaonis (Ehrenberg, 1831) from Puducherry coast", Biochemistry and Biophysics Reports 10 (2017) pp. 39-45.

Li et al., "3D-Printed Biopolymers for Tissue Engineering Application", International Journal of Polymer Science vol. 2014, Article ID 829145, pp. 1-13.

Lin et al., "Functionalized Poly(D,L-lactide) for Pulmonary Epithelial Cell Culture", Advanced Engineering Materials, Mar. 8, 2010.

Lu et al., "Techniques for fabrication and construction of three-dimensional scaffolds for tissue engineering", International Journal of Nanomedicine, Jan. 17, 2013, vol. 8, p. 337-350.

Ma, "Scaffolds for tissue fabrication", Materialstoday, May, 2004, pp. 30-40.

Addad et al., "Isolation, Characterization and Biological Evaluation of Jellyfish Collagen for Use in Biomedical Applications", Marine Drugs, Jun. 7, 2011, vol. 9, pp. 967-983.

Middleton et al., "Synthetic biodegradable polymers as orthopedic devices", Biomaterials 21 (2000) pp. 2335-2346.

Qiao e tal., "Compositional and in Vitro Evaluation of Nonwoven Type I Collagen/Poly-dl-lactic Acid Scaffolds for Bone Regeneration", Journal of Functional Biomaterials, 2015, vol. 6, pp. 667-686.

Rudolph et al., "Surface Modification of Biodegradable Polymers towards Better Biocompatibility and Lower Thrombogenicity", PLOS ONE, Dec. 7, 2015, pp. 1-17.

Sensini et al., "Biofabrication of bundles of poly(lactic acid)-collagen blends mimicking the fascicles of the human Achille tendon", IOP Publishing, Biofabrication, vol. 9 (2017) 015025.

Siow et al., "Plasma Methods for the Generation of Chemically Reactive Surfaces for Biomolecule Immobilization and Cell Colonization—A Review", Plasma Processes and Polymers, Jun. 2006, vol. 3, pp. 392-418.

Yang et al., "Tendon and Ligament Regeneration and Repair: Clinical Relevance and Developmental Paradigm", Birth Defects Res C Embryo Today, Sep. 2013, vol. 99(3). pp. 203-222.

Tham et al., "Surface Modification of Poly (lactic acid) (PLA) via Alkaline Hydrolysis Degradation", Advanced Materials Research, 2014, vol. 970, pp. 324-327. 4p. Abstract Only.

Zagho et al., "Recent Trends in Electrospinning of Polymer Nanofibers and their Applications as Templates for Metal Oxide Nanofibers Preparation", INTECH open science, open minds, 2016, pp. 4-24.

Zhang et al., "Electrospun scaffolds from silk fibroin and their cellular compatibility", Journal of Biomedical Materials Research Part A, 2009, pp. 997-983.

Zhong et al., "Isolation and Characterization of Collagen from the Body Wall of Sea Cucumber Stichopus monotuberculatus", Journal of Food Science, vol. 80, No. 4, 2015, pp. 671-679.

International Search Report and Written Opinion in International Application No. PCT/US2018/000119, dated Dec. 11, 2018.

Liao et al., "In Vitro and in Vivo Degradation of Mineralized Collagen-Based Composite Scaffold: Nanohydroxyapatite/Collagen/Poly(L-lactide)", Tissue Engineering Part A, vol. 10, Issue 1-2, 2004, pp. 73-80.

Cui et al., "Investigation of Drug Release and Matrix Degradation of Electrospun Poly(DL-lactide) Fibers with Paracetanol Inoculation", Biomacromolecules, 2006, 7, pp. 1623-1629.

D. Garlotta "A Literature Review of Poly(Lactic Acid)", Journal of Polymers and the Environment, vol. 9, No. 2, 2001, pp. 63-84.

Haider et al., "A comprehensive review summarizing the effect of electrospinning parameters and potential applications of nanofibers in biomedical and biotechnology", Arabian Journal of Chemistry, 2015, pp. 1-24.

Jamshidi et al., "Thermal characterization of polylactides", Polymer, 1988, vol. 29, pp. 2229-2234.

Katsogiannis et al., "Porous electrospun polycarprolactone (PCL) fibres by phase separation", European Polymer Journal, 2015, 69, pp. 284-295.

Li et al., "Recent advances in stereocomplexation of enantiomeric PLA-based copolymers and applications", Progress in Polymer Science, 2016, 62, pp. 22-72.

D. Lubasova and L. Martinova "Controlled Morphology of Porous Polyvinyl Butyral Nanofibers", Hindawi Publishing Corporation Journal of Nanomaterials, vol. 2011, Article ID 292516, 6 pages.

H. Tsuji "Poly(lactide) Stereocomplexes: Formation, Structure, Properties, Degradation, and Applications", Macroomol. Biosci., 2005, 5, pp. 569-597.

Demirbilek et al., "Oxidative Stress Parameters of L929 Cells Cultured on Plasma-Modified PDLLA Scaffolds", Appl. Biochem Biotechnol (2011) 164:780-792.

(56) References Cited

OTHER PUBLICATIONS

Delguerra et al., "Optimization if the interaction between ethylene-vinyl alcohol copolymers and human endothelial cells", Journal of Materials Science: Materials in Medicine 7, 1996, 8-12.

"4 Figures: Liquid Crystalline Ordered Collagen Substrates for Applications in Tissue Engineering", ACS Biomaterials Science and Engineering, Mar. 2016, https://www.researchgate.net/publication/297595398.

Bishop et al., "Design of an Extrusion System to Optimize the Production of Self-Assembled Collagen Microthreads", Degree of Bachelor of Science Paper, Worcester Polytechnic Institute, Project No. GXP-0508.

Dong et al., "Electrospinning of Collagen Nanofiber Scaffolds from Benign Solvents", Macromol. Rapid Commun. 2009, 30 pp. 539-542.

Gentleman et al., "Mechanical characterization of collagen fibers and scaffolds for tissue engineering", Biomaterials 2003, 24, pp. 3805-3813.

Hwang et al., "Effects of Zero-Length and Non-Zero-Length Cross-Linking Reagents on the Optical Spectral Properties and Structures of Collagen Hydrogels", ACS Appl. Mater Interfaces., 2012, 4, pp. 261-267.

Liu et al., "Novel 3D collagen scaffolds fabricated by indirect printing technique for tissue engineering", Abstract, J. Biomedical Materials Research Part B: Applied Biomaterials, 2008, Issue 2; pp. 519-528.

Oryan et al., "Chemical crosslinking of biopolymeric scaffolds: Current knowledge and future directions of crosslinked engineered bone scaffolds", International Journal of Biological Macromolecules 2018, 107, pp. 678-688.

Punnoose et al., "Electrospun Type 1 Collagen matrices using a novel benign solvent for Cardiac tissue engineering", Journal of Cellular Physiology, 2015.

Salgado et al., "Bone Tissue Engineering: State of the Art and Future Trends", Abstract, Macromolecular Bioscience, 2004, vol. 4, Issue 8, pp. 743-765.

Synthasome X-Repair Technology, FAQs, http://www.synthasome.com/xRepair-technology.php; accessed Mar. 22, 2017.

Tutak et al., "The support of bone marrow stromal cell differentiation by airbrushed nanofibers scaffolds", Abstract, Biomaterials, 2013, vol. 34, Issue 10, pp. 2389-2398.

Wortmann et al., "New Polymers for Needleless Electrospinning from Low-Toxic Solvents", Nanomaterials, 2019, 9, 52, pp. 1-11.

Wright Achilles Tendon Information, http://www.wright.com/healthcare-professionals/graftjacket/applications/achilles-tendon; accessed Nov. 12, 2017.

Zobitz et al., "Determination of the Compressive Material Properties of the Supraspinatus Tendon", Journal of Biomechanical Engineering, 2001, vol. 123, pp. 47-51.

Gabler et al., "In Vivo Evaluation of Different Collagen Scaffolds in an Achilles Tendon Defect Model", BioMed Research International, vol. 2018, Article ID 6432742, pp. 1-11.

Van Kampen et al., "Tissue-engineered augmentation of a rotator cuff tendon using a reconstituted collagen scaffold: a histological evaluation in sheep", Muscles, Ligaments and Tendons Journal, 2013, 3(3): pp. 229-235.

* cited by examiner

BIOPOLYMER COMPOSITIONS, SCAFFOLDS AND DEVICES

CROSS-REFERENCE TO RELATED PATENT APPLICATIONS

This application is a Divisional Application of U.S. application Ser. No. 16/152,963, filed Oct. 5, 2018; which is a Continuation Application of PCT International Application No. PCT/US2018/000119, filed May 15, 2018; which is related to U.S. Provisional Patent Application 62/603,026, filed May 16, 2017, the content of which is hereby incorporated by reference in its entirety.

STATEMENT REGARDING FEDERALLY SUPPORTED RESEARCH

The data presented in this application was supported at least in part by DARPA Contract HR0011-15-9-0006. The US government has certain rights in the invention.

FIELD OF THE INVENTION

The invention relates to compositions of biopolymers, such as collagen, and biodegradable co-polymers, processes for their incorporation into fibers and various scaffolds, and to implantable biocompatible devices prepared with such compositions. More particularly, the invention relates to the production of biocompatible implants and devices useful to support and facilitate the repair of soft tissue injuries, such as torn Achilles', patellar and rotator cuff tendons.

BACKGROUND OF THE INVENTION

Various approaches have been taken to develop components for implantable devices useful as scaffolds to facilitate repair of, or to replace, damaged soft tissues such as tendons and ligaments. Such products must function in a variety of challenging biomechanical environments in which multiple functional parameters must be addressed, among them, for example, are compatibility, strength, flexibility and biodegradability.

Surgical repairs number around 800,000 annually in the US alone for ligaments and tendons of the foot and ankle (for example, Achilles tendon), shoulder (for example, rotator cuff), and knee (for example, anterior cruciate ligament), yet the current standards of care involving the implantation of replacement and supporting elements are generally considered by medical practitioners to be less than optimal.

Leading ligament and tendon repair graft products intended to provide biocompatible soft tissue support scaffolds often involve two decades old technologies that in some instance rely on cadaveric tissue or invasive autografting. Allografts are supply-limited, promote scar formation, may provoke an immune response, and have poorly defined turnover rates, all of which inhibit healing. Autografting also extends surgery time and associated trauma, and often adds a second costly procedure to recover the autologous tissue.

For example, the GRAFTJACKET® Regenerative Tissue Matrix is a sheet-like product formed from donated allograft human dermis, aseptically processed to remove cells and then freeze-dried, http://www.wright.com/footandankleproducts/graftjacket. ArthroFLEX® Decellularized Dermal Allograft is a similar acellular dermal extracellular matrix, https://www.arthrex.com/orthobiologics/arthroflex.

Among these approaches and products are those disclosed by Ratcliffe et al., U.S. Pat. No. 9,597,430 (2017), entitled "Synthetic structure for soft tissue repair". This patent describes various synthetic fibrillar structures, such as a woven mesh and single or multilayer planar fibrillar forms. According to Ratcliffe, these structures can be made from any biocompatible polymer material capable of providing suitable mechanical properties, bioabsorbable or not. Collagen and lactide are mentioned as suitable. Synthasome's "X-Repair" medical device appears to be related and has been granted FDA 510(k) clearance by the US Food and Drug Administration (FDA), (http://www.synthasome.com/xRepair.php).

Another approach is described by Qiao et al., "Compositional and in Vitro Evaluation of Nonwoven Type I Collagen/Poly-dl-lactic Acid Scaffolds for Bone Regeneration," Journal of Functional Biomaterials 2015, 6, 667-686; doi: 10.3390/jfb6030667. This article describes electrospun blends of Poly-d,l-lactic acid (PDLLA) with type I collagen. Various blends are described with ratios of 40/60, 60/40 and 80/20 polymer:collagen blend by weight. Qiao described a co-solvent system and reported that chemical cross linking was essential to ensure long term stability of this material in cell culture. According to Qiao, scaffolds of PDLLA/collagen at a 60:40 weight ratio provided the greatest stability over a five-week culture period.

The use of constructs for muscle implants is described by Lee et al., U.S. Pat. No. 9,421,305 (2016), "Aligned Scaffolding System for Skeletal Muscle Regeneration." The patent discusses an anisotropic muscle implant made of electrospun fibers oriented along a longitudinal axis and cross linked to form a scaffold. Cells are seeded on the fibers to form myotubes. The fibers may be formed from natural polymers and/or synthetic polymers. Natural polymers include, for example, collagen, elastin, proteoglycans and hyaluronan. Synthetic polymers include, for example, polycaprolactone (PCL), poly(d,l-lactide-co-glycolide) (PLGA), polylactide (PLA), and poly(lactide-co-caprolactone) (PLCL). The fibers also may include hydrogels, microparticles, liposomes or vesicles. When blended, the ratio of natural polymer to synthetic polymer is between 2:1 and 1:2 by weight.

Electrospun scaffolds for generation of soft tissue are described by Sensini et al., "Biofabrication of bundles of poly(lactic acid)-collagen blends mimicking the fascicles of the human Achilles tendon," Biofabrication 9 (2017) 015025. Two different blends of PLLA and collagen were compared with bundles of pure collagen.

SUMMARY OF THE INVENTION

The present invention relates to compositions of biopolymers and copolymers that are biocompatible, bioactive, biodegradable and resorbable and to scaffolds and implantable devices made of such compositions and their blends. Such compositions and devices are useful in supporting and facilitating the repair of soft tissue injuries.

A preferred embodiment of such a blend comprises about 10 to 50% biopolymer by weight, preferably about 15 to 40% biopolymer, more preferably about 20 to 35% biopolymer, more preferably about 27.5 to 32.5% biopolymer and most preferably about 30% biopolymer. A copolymer that is also biocompatible, bioactive, biodegradable and resorbable is present in a range of about 50 to 90% by weight.

Preferred types of biopolymers include collagen, extracellular matrix proteins, fibrin, fibrinogen, gelatin and laminin, and combinations thereof. Preferred types of collagen include native, processed, placental and recombinant forms of human, bovine, porcine and marine telocollagen, atelocollagen and mixtures of these types of collagen. A preferred collagen is of bovine origin. Another preferred collagen is Type 1 collagen. Generally, human collagen is preferred, such as from placental tissue or recombinant human collagen, and mixtures thereof. The use of both telocollagen and atelocollagen are contemplated. Sources of marine collagen include jellyfish, sea cucumber and cuttlefish.

In one embodiment of the invention the composition comprises about 10 to 50% collagen by weight, preferably about 15 to 40% collagen, more preferably about 20 to 35% collagen, more preferably about 25 to 35% collagen, more preferably about 27.5 to 32.5% collagen and most preferably about 30% collagen; and a biodegradable copolymer in an amount of about 50 to 90% by weight.

A variety of copolymers are appropriate for the scaffolds and other products and methods described in this specification. Preferred copolymers are biodegradable or resorbable, such as PLLA, PDLA and PDLLA and mixtures thereof. Preferred copolymers are PDLA, low molecular weight PDLLA, mid-molecular weight PDLLA, high molecular weight PDLLA and combinations thereof.

In the compositions of the invention, the biopolymer, for example, collagen and copolymer blends may be formed into fibers. Optionally, the compositions, fibers and other forms of implantable scaffolds may be treated with a chemical cross-linking reagent or not so treated.

In certain embodiments of the invention, particularly with techniques such as electrospinning, fibers range in diameter from about 150 to 4,500 nm, preferably about 400 nm to 2,000 nm, more preferably about 600 nm to 1,500 nm and most preferably about 750 nm to 1,200 nm. In other embodiments, particularly such as melt electrospinning or electrowriting, the average diameter of the fibers is in the range of about from about 1-200 μm, preferably about 10-100 μm, more preferably about 15-50 μm and most preferably about 20 μm.

The invention also relates to fibers prepared as described in the specification and processed in the form of single or multilayer sheet-like scaffolds. In one embodiment, this scaffold is composed of around 1, 2, 3, 4, 5, 6, 7, 8, 9 or 10 or more layers of substantially aligned telocollagen and PDLLA fibers that are each around 0.2 mm thick, with a small section of fibers laying in the transverse plane around the edges to support biaxial strength for suture retention. In another embodiment, this multilayer scaffold is around 4 cm×7 cm×1 mm in size. An alternative embodiment is a single layer scaffold of approximately similar dimensions.

In other aspects of the invention, the compositions according to the present invention may be produced and used to produce scaffolds in the form films, aerosols, droplets, adhesives or porous structures.

Contemplated techniques for producing fibers and various scaffolds include electrospinning, melt electrospinning, electrowriting, extrusion, spraying and 3-D printing.

Yet another aspect of the invention relates to an implantable medical device for supporting the repair of a soft tissue injury in a mammal comprising the composition of claim 1. And in other aspects, the invention relates to methods for facilitating the repair and healing of soft tissue injuries through the surgical implantation of the scaffolds and medical devices described in this specification. These methods, scaffolds and disclosed medical devices are intended for use in mammalian subjects, particularly humans. In one embodiment, the invention relates to a method of repairing the torn Achilles tendon in a human subject, by surgical implanting and fastening a device such that the device spans and provides mechanical support to the repaired area of the tendon.

BRIEF DESCRIPTION OF THE TABLES

Table 1 shows a comparison of peak stress (MPa) and modulus of elasticity (MPa) for several blends of PDLLA and collagen.

DETAILED DESCRIPTION

Definitions

As used in this specification, the term:

"Biopolymer" means a naturally occurring, protein-based macromolecule natively found in connective and other soft tissue and in the extracellular matrix, such as collagen, fibrin, fibrinogen, gelatin and laminin.

"Co-polymer" means a synthetic polymer capable of being dissolved in a benign solvent system and mixed or blended with a biopolymer to add various desirable properties, for example, strength or rigidity as would otherwise be provided by the biopolymer alone.

"High molecular weight PDLLA" means a PDLLA product having an average inherent viscosity (IV) of about 0.55 dL/g-4.5 dL/g or higher.

"Scaffold" means a construct formed from biopolymers and copolymers. Such constructs are preferably substantially aligned fibers formed into layers, mats, sheets and tubes.

"Substantially aligned fibers" means that at least about half of the fibers lying within 15 to 20 degrees of a reference in a scaffold are oriented along a common axis. This is to be interpreted in contrast to randomly oriented fibers.

Objects of the Invention

It is an object of the present invention to provide synthetic fibers and related sheet-like and bundled fiber products for tissue engineering, particularly as soft tissue supports useful in the repair of damaged tendons and ligaments. For example, according to the present invention, a tissue-engineered ligament and tendon scaffold formed of collagen and a biodegradable polymer may be used for repair of a damaged Achilles tendon. It is a further object of the invention to provide synthetic materials having a tensile strength, flexibility, modulus of elasticity and other biomechanical characteristics supportive of native human tendons and ligaments of similar size by way of producing scaffolds with appropriate fiber orientations suited to the particular tissue or defect, such as a partially torn or fully torn Achilles tendon. This invention provides sheet-like and bundled fiber scaffold products that, upon incorporation with host cells to form new tendon-like connective tissue over time, possess tensile strength and modulus that will reinforce a union, such as a rejoined tendon with its torn ends sutured together, while not yielding or failing prior to tissue failure.

Biopolymers:

The biopolymers according to the present invention are biological molecules, preferably proteins from native biological structure and extracellular matrix, that are capable of forming stable extracted products, particularly in the form of scaffolds prepared from biopolymer fibers. These include, by way of example, collagen, elastin, fibrin, fibrinogen and gelatin. Other proteins known to persons skilled in the art may be utilized in the methods of the present invention.

Collagen:

A preferred biopolymer is collagen. Type I Collagen used for biocompatible scaffolds according to the present invention, as well as for current clinical products, generally are extracted from mammalian tissues, particularly bovine and porcine tendons, although recombinant collagen also may be used. Human placenta also is sometimes used for such purposes. Type I collagen has been utilized and commercialized in both research and clinical grade products in two common forms. The more common collagen variants, produced with acid and enzymatic digestion of a tissue with pepsin, are a form of collagen referred to as "atelocollagen," as the product lacks the end-terminal regions of the collagen protein (terminal peptide sequence of "DEKSTGISVP vs. pQLSYGYDEKSTGISVP), whereby the telopeptides are cleaved to aid in recovery of collagen from the parent tissue. Less commonly, collagen is solubilized in mild acid to collect the collagen in solution, maintaining the telopeptides in the monomers of collagen, known as "telocollagen."

Telocollagen has been reported to form a stronger hydrogel relative to gels made of atelocollagen, although their relative strengths when generated as tissue engineered electrospun nanofibers have not been well explored. An experiment was conducted in which telocollagen and atelocollagen were dissolved using 40% acetic acid and electrospun to prepare scaffolds.

The present inventors found that strength of such scaffolds generally was like that of native collagen, however, other properties of the scaffolds were not optimal as shown in Table 1. Accordingly, blends of collagen and various polymers were evaluated and experimental results are described below. Choosing a higher molecular weight PDLLA led to an increase in the peak stress and modulus of elasticity of the constructs. Accordingly, the high molecular weight (HMW) PDLLA is preferred.

fibrin and elastin. Of these, the present inventors have discovered surprising biomechanical and biodegradability results from the blended combination of collagen with polylactic acid, including both its L- and D-isoforms, and particularly so with its amorphous mixture referred to as poly-DL-lactide or PDLLA.

Other copolymers that may be useful for a particular product or device, or when added to a blend of polylactide and collagen, include 1,3-propanediol (PDO), polycaprolactone (PCL), poly(lactic-co-glycolic acid) (PLGA). Other useful polymers and copolymers would be known to persons skilled in the art, for example, poly(glycolic acid), polyesters, trimethylene carbonate, polydioxanone, caprolactone, alkylene oxides, ortho esters, hyaluronic acids, alginates, synthetic polymers from natural fats and oils, and combinations thereof.

With respect to the polylactides, the PLLA isoform alone is relatively strong but brittle rather than elastic. It persists in vivo for about 36 to 48 months. A preferred PLLA is available from Sigma Aldrich. http://www.sigmaaldrich.com/content/dam/sigma-aldrich/articles/material-matters/pdf/resomer-biodegradeable-polymer.pdf.

The PDLA isoform is more elastic and not as brittle, and typically lasts for 12 to 18 months in vivo. A preferred PDLA is available from Sigma Aldrich. http://www.sigmaaldrich.com/catalog/product/SIGMA/67122?lang=en&region=US.

PDLLA lies between PLLA and PDLA in terms of strength and stability and in terms of lifespan in vivo, is in the range of about 18 to 36 months, which is long enough to be resorbed and short enough to avoid encapsulation. PDLLA is an amorphous polymer formed via polymerization of a racemic mixture of L- and D-lactides. The precise composition of the polymer determines its mechanical properties and hydrolysis characteristics.

TABLE 1

Summary of Tensile Testing Results (as statistical mean ± SD).

|  | Bovine Tail Ligaments | PDLLA MW: 75,000-120,000 | | PDLLA HMW: ~450,000 |
|---|---|---|---|---|
|  |  | 75% PDLLA: 25% Telocollagen | 75% PDLLA: 25% Atelocollagen | 80% PDLLA: 20% Telocollagen |
| Peak Stress (MPa) | 5.6 ± 2.2 | 5.2 ± 0.5 | 3.1 ± 0.1 | 13.1 ± 2.1 |
| Modulus of Elasticity (MPa) | 6.1 ± 3.1 | 21.19 ± 3.9 | 19.5 ± 4.7 | 65.6 ± 17.4 |

Acid-soluble (telocollagen) and pepsin-soluble (atelocollagen) freeze dried collagen are appropriate starting materials. A preferred GMP-grade, type I collagen from bovine corium is available in its native form from Collagen Solutions, http://www.collagensolutions.com/products/medical-grade-collagen. The Collagen Solutions' website provides general information on the use and preparation of collagen: http://collagensolutions.com/resource-library#technical-services. Collagen is also available from other suppliers and from various species, for example, Sigma-Aldrich, http://www.sigmaaldrich.com/life-science/metabolomics/enzyme-explorer/learning-center/structural-proteins/collagen.html.

Copolymers:

A wide variety of biodegradable and bioactive copolymers have been considered for use in soft tissue repair, alone or in blends with other polymers, and sometimes including components of native tissue such as, for example, collagen, PDLLA generally displays more favorable degradation properties, due to the level of access of water in the amorphous material and the hydrolytic cleavage of polymer ester bonds. The present inventors have found that PDLLA is surprisingly effective for producing fibers and implantable support devices when blended with Type 1 collagen for the uses described in this specification.

Preferred sources of PDLLA are Polysciences, Evonik and Sigma-Aldrich Co. LLC. For example, PDLLA having an inherent viscosity of 1.6-2.4 dL/g is available from Polysciences, http://www.polysciences.com/default/polydl-lactic-acid-iv-20-28dlg, having an average molecular weight range of about 300,000 to 600,000 Daltons. A lower inherent viscosity PDLLA (IV of 1.3-1.7 dL/g) is available from Evonik, http://healthcare.evonik.com/product/healthcare/en/products/biomaterials/resomer/pages/medical-devices.aspx. A PDLLA with even lower inherent viscosity of 0.55-0.75 dL/g is available from Sigma-Aldrich, http://www.sigmaaldrich.com/catalog/product/sigma/p1691?lang=en&region=US, having molecular weight range of about 75,000 to 125,000 Daltons. Another preferred PDLLA with a GMP level of purity available from Corbion ("PURASORB PDL 45") has a relatively high inherent viscosity of 4.5 dL/g, http://www.corbion.com/static/downloads/datasheets/31d/PURASORB%20PDL%2045.pdf.

Functionalization of Copolymers:

Copolymers may be pretreated with one or more functionalization reagents to prepare the copolymer for cross-linking after extraction of the biopolymer-co-polymer mixture by a production technique such as electrospinning. For example, PDLLA can be functionalized through aminolysis to add amino groups. See, for example, Min et al., "Functionalized Poly(D,L-lactide) for Pulmonary Epithelial Cell Culture," Advanced Engineering Materials 12(4):B101-B112 (2010) at http://onlinelibrary.wiley.com/doi/10.1002/adem.200980031/abstract. Alternatively, PDLLA can be functionalized by plasma treatment to introduce carboxylic and amino groups in the matrix.

As a general approach, by way of example, PDLLA can be functionalized with OH groups prior to electrospinning. PDLLA pellets are soaked in a solution mixture of 10 mM-1M sodium hydroxide dissolved in 10-20% ethanol in milliQ water. The pellets will soak for 10-60 minutes at either room temperature or 37 C. Following incubation, the pellets will be rinsed in milliQ (ultrapurified) water and air dried in a biosafety hood. The functionalized PDLLA chips could then be dissolved in an appropriate electrospinning solution as described in this specification.

Collagen-Copolymer Blends:

In preferred embodiments of the present invention, the tensile strength of scaffolds generated from collagen, for example, telocollagen, and a polymer, for example, PDLLA, are comparable or exceed in biomechanical properties, for example, to that of bovine tail ligaments. However, similar blends made with atelocollagen of different sources may demonstrate a lower tensile strength in some instances, as will be apparent to persons skilled in the art. For example, one batch of electrospun telocollagen with a lactide polymer was nearly 50% stronger than atelocollagen prepared in the same way, that is about 5.5 MPa vs. about 4 MPa. Additionally, using PDLLA of a relatively higher molecular weight (450,000 vs. 75,000-120,000) more than doubled the strength of the construct to about 13.1 MPa.

Both telocollagen and atelocollagen blended with PDLLA were assessed for long-term stability in tissue culture media to ensure suitability for long-term cell culture assays. The collagen-PDLLA scaffolds show acceptable stability in culture media over 28 days of incubation. Like the dry testing results of tensile strength tests, telocollagen blended with PDLLA was also surprisingly stronger mechanically (wet tested) compared to atelocollagen blends with PDLLA.

According to the present invention, a preferred composition comprises about 10 to 50% collagen, preferably about 15 to 40% collagen, more preferably about 20 to 35% collagen, more preferably about 25 to 35% collagen, more preferably about 27.5 to 32.5% collagen and most preferably about 30% collagen by weight; with about 50 to 90% by weight of a lactide copolymer.

Type I collagen of bovine origin is preferred as a biopolymer and a lactide polymer, particularly high molecular weight PDLLA, is preferred as a copolymer. Telocollagen is preferred over atelocollagen. Such compositions exhibit desired biomechanical performance and biostability parameters, such as its wettability properties.

Preparation and Processing of Collagen-Polymer Blends:

The preparation of collagen and lactide polymer blends is described with particularity in the Examples that follow. Generally, both components are dissolved in hexafluoro-2-propanol (HFP). Preferably, no cross-linking reagents are added to the reagent blend prior to its processing into fibers. Optionally, various conventional cross-linking compounds may be blended with the collagen and polymer, or the resulting materials may be cross-linked after electrospinning.

Electrospinning is a preferred processing technique to produce fibers from the inventive compositions, although other approaches will be known to persons skilled in the art. although other approaches to separating the blend from the solvent system will be known to persons skilled in the art, for example, pneumatospinning, extrusion, cold drawing or casting. Electrospinning is a fiber production technology that draws charged threads of polymer solutions or polymer melts into fibers of various diameters and lengths. Electrospinning of collagen has been widely described as a one-step process for the formation of fibrous materials that mimic native tissue structure. Electrospinning equipment is conventional and readily available from product brands such as Nanospinner, Elmarco and SprayBase. Electrospinning shares characteristics of both electrospraying, conventional solution dry spinning, extrusion, or pulltrusion of fibers.

Characteristics of Fibers Made of the Inventive Compositions:

Polymer blends of preferred embodiments as described above and in the Examples below were used to product electrospun fibers. Preferred fiber diameters are in the range from about 150-4,500 nm, preferably about 400 nm to 2,000 nm, more preferably about 600 nm to 1,500 nm and most preferably about 750 nm to 1,200 nm. A preferred range of strength for the fibers is about 4 to 16 MPa. The preferred Modulus of Elasticity preferably is substantially like that of human tendons, particularly the Achilles Tendon, which is about 35-750 MPa. Within that range, about 35-200 MPa for the fibers is preferred. Also, a strain to failure of 50-200% (0.5 to 2.0 mm/mm) as tensile tested at 1 mm/s in hydrated condition is preferred.

Preparation of Scaffolds:

A preferred biopolymer structure is a scaffold that is appropriate for implantation as a support to help repair a soft tissue injury or as a replacement for such tissue, for example, a tendon or ligament. Scaffolds appropriate for implantation may be made by various techniques. For example, scaffolds in the form of sheets may be produced by electrospinning collagen and copolymer blends onto a high-speed drum (surface speed of around 1 to 20 m/s, for example at about 18 m/s). Fibrous sheets are readily peeled from the drum of an electrospinning apparatus in sheets or otherwise removed by conventional techniques.

Scaffolds can be vacuum dried after electrospinning to remove residual solvents. For example, the sheets preferably are stored for about 1-3 days under vacuum at about 30-37° C. to remove residual processing solvents. The sheets then may be cut or oriented to generate secondary and tertiary structures and, optionally, may be laminated through welding or suturing/sewing.

Such sheets may be laminated through welding or suturing or sewing. In general, the sheets of electrospun material are stacked. In general, the sheets of electrospun material are stacked. Then heat (30-100° C., for example about 60° C.) is locally applied to join them. Additional material may be added into welds to reinforce material to aid in suture retention. Optionally, an adhesion barrier may be included which would be comprised of a pure polymer backing (facing away from tendon) to prevent extrinsic cell infiltration. The polymer layer may be electrospun, cast, foamed, extruded, or produced by other conventional techniques.

With respect to scaffolds prepared from the fibers, the scaffold's wettability preferably shows stability in culture media over about 28 days of incubation at 37° C. with 100% humidity in 5% $CO_2$. Generally, seeded cells should show robust cell attachment, preferably with more than half the cells attaching to the scaffold, as described in the Examples. Initial retention of growth factors preferably is substantially like that of human tendon, particularly the Achilles Tendon.

Persons skilled in the art will be aware of appropriate techniques for the fabrication, production and construction of three-dimensional scaffolds according to the compositions and methods of the present invention. Such techniques are described, for example, by Bhatia et al., "Microfabricated biopolymer scaffolds and method of making same," Published US Patent Application US20050008675A1; Hoque et al., "Extrusion based rapid prototyping technique: An advanced platform for tissue engineering scaffold fabrication," Biopolymers 97: 83-93, 2012, https://doi.org/10.1002/bip.21701; Lu et al, "Techniques for fabrication and construction of three-dimensional scaffolds for tissue engineering," Int. J Nanomedicine. 2013; 8: 337-350; Li et al, "3D-Printed Biopolymers for Tissue Engineering Application," International Journal of Polymer Science, Volume 2014, Article ID 829145, http://dx.doi.org/10.1155/2014/829145; and Ma, "Scaffolds for tissue fabrication," Materials Today Volume 7, Issue 5, May 2004, Pages 30-40.

Additional Processing of Scaffolds:

Generally, when a co-polymer is functionalized to provide amino groups prior to dissolving in the solvent system, the biopolymer and co-polymer may be crosslinked with glyoxal or aldehyde crosslinking reagents after its extraction into a scaffold. If the co-polymer is functionalized with carboxyl groups, then EDC and other carbodiimides may be used for crosslinking. Isocyanates react with both OH groups and amines. Therefore, isocyanate-based crosslinkers may be used to crosslink the OH groups to each other within, for example, the functionalized PDLLA (linking an OH group to another OH group) to improve media stability and/or strength. Isocyanates also may be used to link collagen to OH groups in functionalized PDLLA via the NH2 group (that is, amine group) from the collagen. Additionally, photo-crosslinkers can be used.

Additionally, the biopolymer can be physically post-processed such as by thermal annealing with or without mechanical drawing, or by a mixture of annealing, drawing, and relaxation cycles. These physical post-processing steps can be applied to temper or otherwise alter the material properties of the resulting scaffold, such as by changing fiber diameter, fiber alignment, and void fraction or porosity of the resulting scaffold.

Implantable Devices:

As described above, the present invention is directed to the production and use of synthetic fibers and related sheet-like and bundled fiber products for tissue engineering, particularly as soft tissue supports useful in the repair of damaged tendons and ligaments. For example, according to the present invention, a tissue-engineered ligament and tendon scaffold formed of elongated fibers of collagen and a biodegradable copolymer may be used for repair of a damaged Achilles tendon. Scaffolds according to the invention may be in the form of a mat, tube, single layer sheet and multilayered sheet.

In a preferred embodiment, the invention relates to fibers prepared as described above, and processed in the form of single or multilayer sheet-like scaffolds. In one embodiment, this scaffold is composed of around 1, 2, 3, 4, 5, 6, 7, 8, 9 or 10 or more layers of aligned telocollagen and PDLLA fiber blends that are each around 0.4 mm thick, with a small section of fibers laying in the transverse plane around the edges to support biaxial strength for suture retention. In another embodiment, this multilayer scaffold is around 4 cm×7 cm×1 mm in size. An alternative embodiment is a single layer scaffold of approximately similar dimensions.

Generally, scaffolds according to the present invention are easy to handle in the operating room or other acute care setting and are readily cut and shaped to fit and support a given soft tissue site. Scaffolds may be placed in proximity to or in contact with tissue that has torn and been repaired, for example with sutures, suture anchors or surgical glue. The scaffold provides support and reinforcement of soft tissues, such as tendons and ligaments, including Achilles tendon, rotator cuff, patellar tendon, biceps tendon, and quadriceps tendons, The scaffold shares some of the mechanical stress and load with the repaired tissue.

The fibrous and, optionally, sheet-like structure of the scaffold permit host cell and tissue ingrowth and also vascularization of the scaffold. Over time, the scaffold is absorbed and replaced by a patient's own tissues through a remodeling process or is otherwise dissolved, degraded and ultimately removed. Scaffolds may be packaged in sterile containers either individually or in pairs or in larger quantities.

A. Sheets. Sheets can be prepared in a variety of standard sizes such as 1×2, 2×2, 3×3, 2×4, 4×6, 6×9 cm and cut to customize size and shape.

B. Mesh. A randomly aligned material can be fabricated as a non-woven mesh with isotropic fibers and isotropic material strength in standard sizes such as 1×2, 2×2, 3×3, 2×4, 4×6, 6×9 cm and cut to customize size and shape.

C. Wraps. Sheets or meshes can be used as an onlay or wrapped around a tissue defect.

D. Sutures. The material may be synthesized as threads, yarns or other monofilament and multifilament strands for use as a suture to hold, locate, support or reinforce a surgical site.

E. Internal brace. The material may be synthesized as threads, yarns or other monofilament and multifilament strands for use as a suture to brace, support or reinforce a surgical site to prevent joint overextension and reduce risk of reruptures.

EXAMPLES

Example 1: Preparing 10% Atelocollagen-90% PDLLA and Electrospinning Fibers

In a glass 5 mL v-vial (Wheaton), 36.2 mg of freeze-dried atelocollagen and 324.5 mg Poly(d,l-lactide) (PDLLA) were dissolved in 3 mL Hexafluoro-2-Propanol (HFP). Collagen was obtained from Collagen Solutions (San Jose, Calif.) and PDLLA was obtained from Polysciences, Inc. The vial was placed on a rocking platform shaker, such as from VWR until the reagents dissolved. The solution was then electrospun using a 50 mm/2 inch drum disk with electric motor; a 5 mL glass syringe with glass luer having a diameter of 11.7 mm; a 2 in, 18 gauge all stainless steel needle and a 100 mm needle tip. The flow rate was 1.5 mL/hr, and +17.8 kV were applied to the needle. A 90 min spin time was utilized at 21° C. and a relative humidity below the lower limit of detection of 25%. The resulting fibers were scraped from the drum and placed in a desiccator.

Example 2: Preparing 30% Atelocollagen-70% PDLLA and Electrospinning Fibers

In a 5 mL v-vial, 72.3 mg atelocollagen and 168 mg PDLLA were dissolved in 2 mL HFP, and then dissolved, generally according to Example 1. Then, the solution was electrospun using a 25 mm/1 in drum disk with electric motor, a 2 mL glass syringe with glass luer having a diameter of 8.9 mm; a 2 inch, 18 gauge all stainless steel needle and a 100 mm needle tip. The flow rate was 1.5 mL/hr and +17.0-17.1 kV were applied to the needle. A 60 min spin time was utilized at 22.2° C. and a relative humidity less than 25%.

Example 3: Preparing 15% Telocollagen-85% PDLLA and Electrospinning Fibers

In a 5 mL v-vial, 36.0 mg telocollagen and 204 mg PDLLA were dissolved in 2 mL HFP, and then dissolved, generally according to Example 1. Then, the solution was electrospun using a 25 mm/1 in drum disk with electric motor, a 2 mL glass syringe with glass luer having a diameter of 8.9 mm; a 2 inch, 18 gauge all stainless steel needle and a 100 mm needle tip. The flow rate was 1.5 mL/hr and +17.8 were applied to the needle. A 60 min spin time was utilized at 22.1° C. and a relative humidity less than 25%.

Example 4: Preparing 35% Telocollagen-65% PDLLA and Electrospinning Fibers

In a 5 mL v-vial, 84.0 mg telocollagen and 156 mg PDLLA were dissolved in 2 mL HFP, and then dissolved, generally according to Example 1. Then, the solution was electrospun using a 25 mm/1 in drum disk with electric motor, a 2 mL glass syringe with glass luer having a diameter of 8.9 mm; a 2 inch, 18 gauge all stainless steel with nickel needle and a 100 mm needle tip. The flow rate was 1.5 mL/hr and +18.0 were applied to the needle. A 55 min spin time was utilized at 22.1° C. and a relative humidity less than 25%.

Example 5: Preparing 25% Telocollagen-75% PDLLA and Electrospinning Fibers

A solution of 12% telocollagen in HFP was combined with 12% PDLLA in HFP; each were dissolved in separate vials. The collagen was prepared by dissolving 60.6 mg telocollagen powder (Collagen Solutions) in 0.5 mL HFP in a 5 mL vial. The PDLLA was prepared by dissolving 239.1 mg PDLLA in 2 mL HFP in a 5 mL vial. Both solutions were placed on a rocking shaker platform at maximum speed and tilt for 2½ hours. 250 uL of the 12% (w/v) collagen solution were mixed with 750 uL of the 12% (w/v) PDLLA solution and the two were mixed on the platform shaker for 20 minutes. Then, the solution was electrospun using a 25 mm/1 in drum disk with electric motor, a 1 mL glass syringe with glass luer having a diameter of 8.9 mm; a 2 inch, 18 gauge needle and a 100 mm needle tip. The flow rate was 1.0 mL/hr and +20.0 to 20.1 KV were applied to the needle. A 55 min spin time was utilized at 23.2° C. and a relative humidity of 48%.

Example 6: Preparation of Collagen-Polymer Scaffolds

Five sheets that are each about 0.2 mm thick are laminated by welding with a soldering iron at about 100° C. or with a short pulse of heat from an impulse sealer. Additional fibers oriented orthogonally are sealed into the weld to provide reinforcement for suture retention. Average load to pull one suture through the weld is about 28.3 N, and the peak stress is 4.1 MPa.

Example 7: Seeding of Human Tenocytes on a Scaffold of Electrospun Fibers

Human tenocytes ($5 \times 10^4$ cells/well) were suspended in serum free media and then seeded on the scaffolds prepared according to Example 6, above. After 15, 30, and 60 minutes in culture, the plates were gently shaken and the non-attached cells were removed. The number of non-attached cells suspended in each well was counted, and the percentage of attached cells on each scaffold disk was determined based on the total number of cells seeded. Over 50% of the cells remained attached.

While certain exemplary embodiments have been described above in detail, it is to be understood that such embodiments are merely illustrative of and not restrictive of the broad invention. It should be recognized that the teachings of the invention apply to a wide variety of compositions and devices produced from the formulations and compositions described. Persons of skill in the art will recognize that various modifications may be made to the embodiments of the invention described above, without departing from its broad inventive scope. Thus, it will be understood that the invention is not limited to the embodiments or arrangements disclosed, but is rather intended to cover any changes, adaptations or modifications which are within the scope and spirit of the invention as defined by the appended claims.

REFERENCES

All documents identified in this specification, including the following articles, are incorporated by reference in their entireties.

Addad et al., "Isolation, characterization and biological evaluation of jellyfish collagen for use in biomedical applications," Mar Drugs. 2011; 9(6):967-83. doi: 10.3390/md9060967. Epub 2011 Jun. 7.

Cheng et al., "Isolation, Characterization and Evaluation of Collagen from Jellyfish Rhopilema esculentum Kishinouye for Use in Hemostatic Applications," PLoS One. 2017 Jan. 19; 12(1):e0169731. doi: 10.1371/journal.pone.0169731. eCollection 2017.

Hochleitner et al., "Melt Electrowriting of Thermoplastic Elastomers," Macromol Rapid Commun. 2018 Apr. 14:e1800055. doi: 10.1002/marc.201800055.

Hochleitner et al., "Melt electrowriting below the critical translation speed to fabricate crimped elastomer scaffolds with non-linear extension behaviour mimicking that of ligaments and tendons," Acta Biomater. 2018 May; 72:110-120. doi: 10.1016/j.actbio.2018.03.023. Epub 2018 Mar. 17.

Hrynevich et al., "Dimension-Based Design of Melt Electrowritten Scaffolds," Small. 2018 Apr. 30:e1800232. doi: 10.1002/smll.201800232.

Huanga et al., "A review on polymer nanofibers by electrospinning and their applications in nanocomposites," Composites Science and Technology, 63(15):2223-2253 (2003).

Krishnamoorthi et al., "Isolation and partial characterization of collagen from outer skin of Sepia pharaonis (Ehrenberg, 1831) from Puducherry coast," Biochem Biophys Rep. 2017 Feb. 27; 10:39-45. doi: 10.1016/j.bbrep.2017.02.006. eCollection 2017 July Middleton et al., "Synthetic biodegradable polymers as orthopedic devices," Biomaterials 21:2334-2346 (2000).

Rudolph et al., "Surface Modification of Biodegradable Polymers towards Better Biocompatibility and Lower Thrombogenicity," http://journals.plos.org/plosone/article?id=10.1371/journal.pone.0142075.

Shekhar et al., "Electrospun Collagen: A Tissue Engineering Scaffold with Unique Functional Properties in a Wide Variety of Applications" Journal of Nanomaterials 2011 Article ID 348268.

Shoseyov et al., US 2012/0273993 entitled "Method of Generating Collagen Fibers."

Siow et al., "Plasma Methods for the Generation of Chemically Reactive Surfaces for Biomolecule Immobilization and Cell Colonization—A Review," http://plasmatechsystems.com/about/pubs/Plasma%20Methods%20for%20Chemically%20Reactive%20Surfaces%20for%20Biomolecule%20Immobilization.pdf Tham et al., "Surface Modification of Poly (lactic acid) (PLA) via Alkaline Hydrolysis Degradation," https://www.researchgate.net/profile/Zuratul_Abdul_Hamid/publication/277306838_Surface_Modification_of_Poly_lactic_acid_PLA_via_Alkaline_Hydrolysis_Degradation/links/5566afd408aeab77721cbfa7/Surface-Modification-of-Poly-lactic-acid-PLA-via-Alkaline-Hydrolysis-Degradation.pdf Zagho et al., "Recent Trends in Electrospinning of Polymer Nanofibers and their Applications as Templates for Metal Oxide Nanofibers Preparation," Chapter 1 in "Nanotechnology and Nanomaterials" edited by Haider et al., ISBN 978-953-51-2822-9, Print ISBN 978-953-51-2821-2, Published: Dec. 21, 2016 under CC BY 3.0 license.

Zhang, Kuihua, et al. "Electrospun scaffolds from silk fibroin and their cellular compatibility." Journal of Biomedical Materials Research Part A 93.3 (2010): 976-983.

Zhong et al., "Isolation and characterization of collagen from the body wall of sea cucumber *Stichopus monotuberculatus*," J Food Sci. 2015 April; 80(4):C671-9. doi: 10.1111/1750-3841.12826. Epub 2015 Mar. 21.

The invention claimed is:

1. A method for facilitating repair of a damaged tendon, comprising the step of fastening an implantable to the tendon such that the scaffold provides mechanical support the area of tendon repair, wherein the implantable scaffold comprising
  an annealed biopolymer sheet having substantially aligned electrospun biopolymer fibers;
  wherein the biopolymer fibers comprise about 20 to 35% by weight of Type I collagen and about 65 to 80% by weight of PDLLA having an average molecular weight of about 300,000 to about 600,000 Daltons;
  wherein the biopolymer fibers are not cross-linked: and
  wherein the biopolymer sheet of the ligament and tendon repair device exhibits one or more of the characteristics selected from the group consisting of:
  (i) a range of tensile strength of about 4 to 16 MPa,
  (ii) a modulus of elasticity of about 35 to 750 MPa,
  (iii) a peak stress of about 11 to 15.2 MPa,
  (iv) a strain to failure of 50-200% (0.5 to 2.0 mm/mm) as tensile tested at 1 mm/s in hydrated condition, and
  (v) the biopolymer fibers of the biopolymer sheet have an average diameter of about 700 nm to about 1,500 nm.

2. The method of claim 1, wherein the tendon is selected from the group consisting of Achilles tendon, rotator cuff tendon, patellar tendon, biceps tendon and quadriceps tendon.

* * * * *